(12) United States Patent
Suzuki

(10) Patent No.: US 7,493,245 B2
(45) Date of Patent: Feb. 17, 2009

(54) METHOD AND APPARATUS FOR SIMULATING IMAGE OF TWISTED YARN

(75) Inventor: Noriyuki Suzuki, Wakayama (JP)

(73) Assignee: Shima Seiki Manufacturing Limited, Wakayama (JP)

( * ) Notice: Subject to any disclaimer, the term of this patent is extended or adjusted under 35 U.S.C. 154(b) by 800 days.

(21) Appl. No.: 10/537,302

(22) PCT Filed: Dec. 2, 2003

(86) PCT No.: PCT/JP03/15373

§ 371 (c)(1), (2), (4) Date: Jun. 2, 2005

(87) PCT Pub. No.: WO2004/051519

PCT Pub. Date: Jun. 17, 2004

(65) Prior Publication Data

US 2006/0025881 A1     Feb. 2, 2006

(30) Foreign Application Priority Data

Dec. 3, 2002    (JP)  ............... 2002-351826

(51) Int. Cl.
    *G06F 9/455*      (2006.01)
(52) U.S. Cl. ............... 703/6; 700/141; 700/139; 700/131; 66/232
(58) Field of Classification Search ............... 703/6, 703/2, 1; 700/141, 139, 131; 66/232; 28/103; 428/36.1; 435/395; 57/288, 205
See application file for complete search history.

(56) References Cited

U.S. PATENT DOCUMENTS 4,402,178 A * 9/1983 Negishi et al. ............... 57/205

4,523,428 A * 6/1985 Negishi et al. ............... 57/288

(Continued)

FOREIGN PATENT DOCUMENTS

EP     0 640 707 A1     3/1995

(Continued)

OTHER PUBLICATIONS

Dipl.-Ing. (FH) Christiane Szczesny et al., "Simulation of Fancy Yarns on the Screen", ITB Fabric Forming Mar. 1991, pp. 73-74.

(Continued)

*Primary Examiner*—Kandasamy Thangavelu
(74) *Attorney, Agent, or Firm*—Harness, Dickey & Pierce, P.L.C.

(57) ABSTRACT

An object of the invention is to provide a simulation method and a simulation apparatus of the image of a twisted yarn capable of forming an image close to the actuality. When the images of twisted threads (1, 2) are inputted, abstracted models (3, 4) of the twisted yarns having a constant elliptical cross-section are obtained as shown in (b). A projected image (6) of the twisted yarns as shown in (c) is obtained when the models shown in (b) are viewed from the right side and one of two abstracted models (3, 4) located on the left side is concealed. The projected image (6) of the twisted yarns is formed by copying the images of the twisted yarns (1, 2) on to parts corresponding to the abstracted models (3, 4) of respective twisted yarns.

14 Claims, 12 Drawing Sheets

U.S. PATENT DOCUMENTS

| | | | |
|---|---|---|---|
| 5,557,527 A | 9/1996 | Kotaki et al. | 700/131 |
| 5,680,333 A | 10/1997 | Jansson | |
| 6,880,367 B2 | 4/2005 | Suzuki | 66/232 |
| 7,330,772 B2 * | 2/2008 | Suzuki | 700/139 |
| 2004/0224406 A1 * | 11/2004 | Altman et al. | 435/395 |
| 2005/0039495 A1 * | 2/2005 | Suzuki | 66/232 |
| 2006/0029759 A1 * | 2/2006 | Hannigan et al. | 428/36.1 |
| 2007/0156277 A1 * | 7/2007 | Suzuki | 700/141 |
| 2007/0240292 A1 * | 10/2007 | Maeiwa | 28/103 |

FOREIGN PATENT DOCUMENTS

| | | |
|---|---|---|
| EP | 0640707 A1 | 3/1995 |
| JP | 04-82936 A | 3/1992 |
| JP | 07-070890 A | 3/1995 |
| WO | WO 98/16823 A1 | 4/1998 |
| WO | WO 03/032203 A1 | 4/2003 |

OTHER PUBLICATIONS

S.A. Grishanov et al., "The Simulation of the Geometry of Two-component Yarns, Part I: The Mechanics of Strand Compression: Simulating Yarn Cross-section Shape", J. Text Inst. 1997, 88 Part 1, No. 2, pp. 118-131.

International Preliminary Examination Report and English translation thereof.

* cited by examiner

FIG. 5
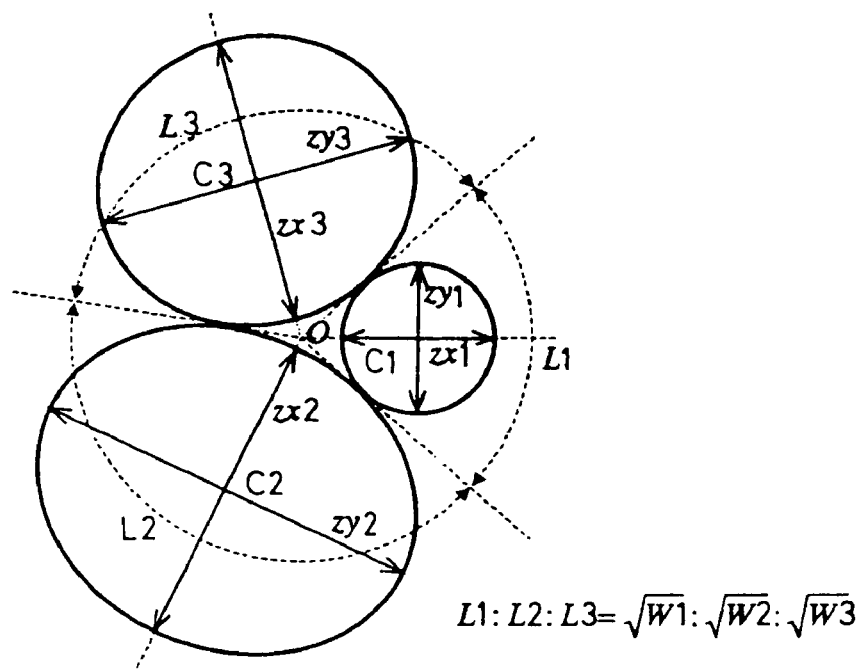
$L1 : L2 : L3 = \sqrt{W1} : \sqrt{W2} : \sqrt{W3}$
FIG. 6
(a)
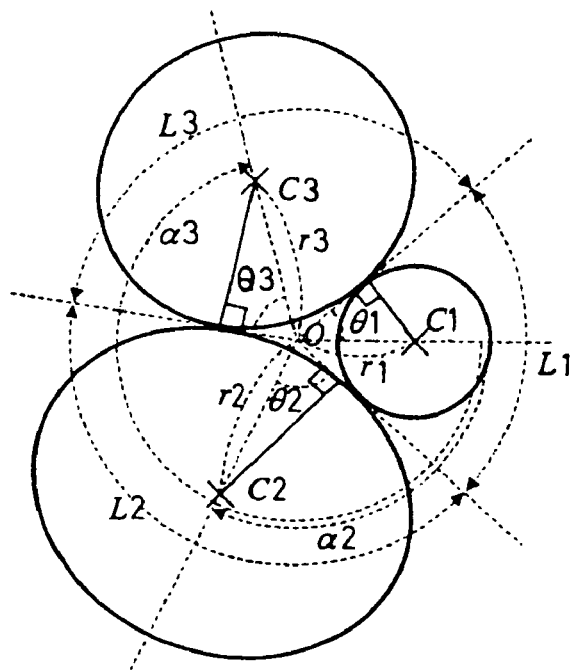
(b)
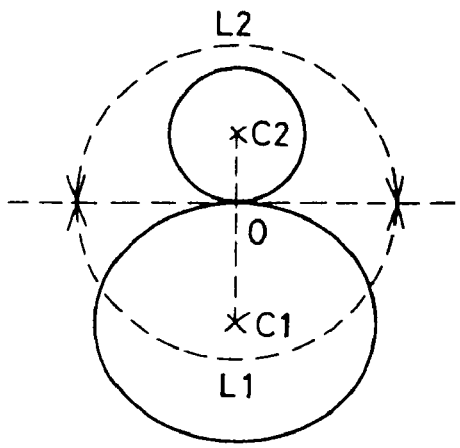

FIG. 15
Yarn 1
(a) 
Yarn 2
(b) 
Yarn 3
(c) 
Yarn 4
(d) 
Yarn 1+2
(e) 
Yarn 1+2+3
(f) 
Yarn 1+2+3+4
(g) 

METHOD AND APPARATUS FOR SIMULATING IMAGE OF TWISTED YARN

TECHNICAL FIELD

The present invention relates to a method and apparatus for simulating an image of a twisted yarn, with which it is possible to simulate and display an image obtained when a plurality of yarns are twisted to produce a twisted yarn.

BACKGROUND ART

Conventionally, it has been possible to simulate an image of a knitting fabric or a weaving fabric by assuming a yarn that is to be used without actually manufacturing the fabric (see Japanese Unexamined Patent Publication JP-A 07-70890 and WO98/16823, for example). Also, the applicant has filed Japanese Patent Application No. 2001-310559 that relates to a method and an apparatus in which image data of a knitting yarn is input to simulate an image of a knitting fabric knitted by using the knitting yarn. The technique of this application makes it possible to easily simulate an image of a knitting fabric knitted by using a fuzzy knitting yarn of an irregular shape called "fancy yarn".

Compared with a weaving fabric, a knitting fabric generally uses a thicker yarn and has coarser knitting stitches. For this reason, the use of a fancy yarn as a knitting yarn can realize, for example, a peculiar design effect or feeling. For a fancy yarn, a twisted yarn is sometimes used that is produced by twisting a plurality of yarns. A product also has been introduced that can display an image of a fancy yarn weaving fabric or knitting fabric using a fancy yarn or a yarn obtained by further twisting fancy yarns (see Chrittiane Szezesny and other two authors, "Simulation of Fancy Yarns on the Screen", in Fabric Forming, ITB, March 1991, pp. 73-74, for example). With the use of an image of a twisted yarn in the technique proposed in Japanese Patent Application No. 2001-310559, it is possible to simulate an image of a knitting fabric using the twisted yarn. Also, it has been reported that when yarns are twisted, the cross-section shapes of the yarns are compressed (see A. Grishanov and other four authors, "The Simulation of the Geometry of Two-component Yarns Part I: The Mechanics of Strand Compression: Simulating Yarn Cross-section Shape", in J. Text. Inst., Textile Institute, 88 Part 1 No. 2, 1997, pp. 118-131, for example).

FIGS. 1 to 5 of the article (Chrittiane Szezesny and other two authors, "Simulation of Fancy Yarns on the Screen", in Fabric Forming, ITB, March 1991, pp. 73-74) show images of (1) a single fancy yarn, (2) a fancy yarn obtained by twisting a plurality of such fancy yarns, and (3) a fabric using such fancy yarns. Some figures do not include (2) a fancy yarn obtained by twisting. Although it is not clarified how these images are simulated, one of the authors of the article (Chrittiane Szezesny and other two authors, "Simulation of Fancy Yarns on the Screen", in Fabric Forming, ITB, March 1991, pp. 73-74) is listed as an inventor of WO98/16823, and thus it is presumed that the simulation is performed by using the technique disclosed in WO98/16823.

In the technique disclosed in WO98/16823, a three-dimensional model of a three-dimensionally scanned yarn is formed by combining the position coordinates of a plurality of points set on the surface and the orientation of the surface region including the points. A numerical model is processed to calculate three-dimensional spatial coordinates through which the central line of the yarn passes in a weaving fabric or a knitting fabric, and the central line of the three-dimensional model of the yarn is deformed in accordance with the central line of the numerical model. At that time, the points set on the surface of the three-dimensional model of the yarn are also displaced in accordance with the central line, so that an image of the yarn is displayed as a collection of such points, and the simulation is thus performed.

When the three-dimensional model of the yarn is created, it is expected that an image of the actual yarn is faithfully reflected by narrowing a gap between the points on the surface to make the density therein high. However, when the number of points becomes large, a time necessary for processing an image becomes long. Furthermore, since a fancy yarn is characterized by comprising, for example, fine fuzz that exists in an irregular manner and the fuzz sticks outward on the surface, the fancy yarn is difficult to reflect on a three-dimensional model by a method such as described above.

DISCLOSURE OF INVENTION

It is an object of the invention to provide a method and apparatus for simulating an image of a twisted yarn, with which an image close to the real can be created.

The invention is a method for simulating an image of a twisted yarn in which twisting of a plurality of yarns is simulated and an image of a twisted yarn is formed, the method comprising:

an image input step of inputting images of the plurality of yarns used for twisting, each in a form of an extended line, an abstracting step of producing, based on the images that have been input in the image input step, an abstracted model of each of the yarns that extends in one direction and has a certain cross-section of a predetermined mathematizable shape to abstract each of the yarns, and of setting correspondence between each of the abstracted models and the images, a twisting step of twisting, according to a predetermined condition, the abstracted models of the plurality of yarns that have been abstracted in the abstracting step and of producing an abstracted model of a twisted yarn in a form extending along a central axis thereof, a projection step of projecting the abstracted model of the twisted yarn that has been produced in the twisting step onto a plane that is in parallel with the central axis, and an image reproduction step of reproducing, based on the correspondence that has been set in the abstracting step, the images of the yarns on corresponding projected images of the abstracted models of the yarns included in the abstracted model of the twisted yarn that has been projected onto the plane in the projection step.

Furthermore, the invention is characterized in that in the abstracting step, cross-section shapes of the plurality of yarns input in the image input step are abstracted as round shapes to produce the abstracted models of the yarns, and the twisting step comprises:

a cross-section arrangement step of setting an arrangement reference point with respect to the twisted yarn, and of arranging the cross-section shapes of the abstracted models of the yarns produced in the abstracting step around the arrangement reference point, a cross-section rotation step of rotating a combination of the cross-section shapes arranged in the cross-section arrangement step around the central axis of the twisted yarn while displacing the arrangement reference point set in the cross-section arrangement step along the central axis, according to a predetermined condition, and an external shape production step of producing external shapes of the abstracted models of the yarns along the central axis of the twisted yarn as a locus formed by rotating the cross-section shapes in the cross-section rotation step.

Furthermore, the invention is characterized in that in the abstracting step, the cross-section shapes are flattened according to a predetermined condition.

Furthermore, the invention is characterized in that in the cross-section arrangement step, a cross-section region around the arrangement reference point of the twisted yarn is divided in accordance with ratios of square roots of diameters of the abstracted models of the yarns, and the round cross-section shapes of the abstracted models of the yarns are flattened in such a manner that the cross-section shapes of the adjacent yarns contact each other on a boundary line between the divided regions.

Furthermore, the invention is characterized in that in the cross-section arrangement step, when the ratio of the square root of an abstracted model of one yarn occupies a half or more of an entire portion, adjustment is performed so that the abstracted model of this yarn occupies only a half of the cross-section region around the arrangement reference point.

Furthermore, the invention is characterized in that in the cross-section arrangement step, the arrangement reference point is set at a position different from the central axis of the twisted yarn, and in the cross-section rotation step, the arrangement reference point is also rotated around the central axis of the twisted yarn.

Furthermore, the invention is characterized in that in the cross-section arrangement step, the arrangement reference point is set in such a manner that the central axis of the twisted yarn is at a position that is obtained as an weighted average of relative positions of central positions of the cross-section shapes of the abstracted models of the yarns with respect to the arrangement reference point, using the diameters of the cross-section shapes as the weight.

The invention is further characterized in that, with respect to a fuzzy yarn, in the abstracting step, the abstracted model of the yarn is produced separately for a fuzz portion on an outer circumferential side and for a yarn main portion on an inner circumferential side excluding the fuzz, in the cross-section arrangement step, the abstracted model of the yarn is arranged around the arrangement reference point based on a cross-section shape of the yarn main portion, and a cross-section shape of the fuzz portion is arranged around the cross-section shape of the yarn main portion not so as to exceed abstracted models of adjacent yarns, and in the image reproduction step, an image of the yarn is reproduced on the abstracted model of the yarn projected on the plane separately for the fuzz portion and for the yarn main portion from the image.

Furthermore, the invention is characterized in that in the abstracting step, the correspondence between the abstracted model and the image of each of the yarns is set so that with respect to a longitudinal direction of the abstracted model, an entire length or a part of the image is set to be a section to be used, and so that after linking is performed from one edge to the other edge of the section to be used, linking is repeated by resuming from the one edge.

The invention is further characterized in that by using the image of the twisted yarn produced by reproducing the images of the yarns on the abstracted models of the yarns included in the abstracted model of the twisted yarn projected on the plane in the image reproduction step, an image of a knitting fabric knitted by using the twisted yarn is simulated.

In addition, the invention is a program for letting a computer execute the method for simulating an image of a twisted yarn described in any one of the aspects above.

In addition, the invention is a computer-readable storage medium storing a program read by a computer to execute the method for simulating an image of a twisted yarn described in any one of the aspects above.

In addition, the invention is an apparatus for simulating an image of a twisted yarn, in which twisting of a plurality of yarns is simulated and an image of a twisted yarn is formed, the apparatus comprising:

image input means for inputting images of the plurality of yarns used for twisting, each in a form of an extended line, abstracting means for producing, based on the images that have been input in the image input means, an abstracted model of each of the yarns that extends in one direction and has a certain cross-section of a predetermined mathematizable shape to abstract each of the yarns, and for setting correspondence between each of the abstracted models and the images, twisting means for twisting, according to a predetermined condition, the abstracted models of the plurality of yarns that have been abstracted in the abstracting means and of producing an abstracted model of a twisted yarn in a form extending along a central axis thereof, projection means for projecting the abstracted model of the twisted yarn that has been produced in the twisting means onto a plane that is in parallel with the central axis, and image reproduction means for displaying a state in which the images of the yarns are reproduced, based on the correspondence that has been set by the abstracting means, on corresponding projected images of the abstracted models of the yarns included in the abstracted model of the twisted yarn that has been projected onto the plane by the projection means.

Furthermore, the invention is characterized in that the abstracting means abstracts the cross-section shapes of the plurality of yarns input by the image input means as round shapes, and the twisting means comprises:
  cross-section arrangement means for setting an arrangement reference point with respect to the twisted yarn, of arranging the cross-section shapes of the abstracted models of the yarns produced by the abstracting means around the arrangement reference point, and for flattening the cross-shapes according to a predetermined condition,
  cross-section rotation means for rotating a combination of the cross-section shapes arranged by the cross-section arrangement means around the central axis of the twisted yarn while displacing the arrangement reference point set by the cross-section arrangement means along the central axis according to a predetermined condition, and
  external shape production means for producing external shapes of the abstracted models of the yarns along the central axis of the twisted yarn as a locus formed by rotating the cross-section shapes by the cross-section rotation means.

BRIEF DESCRIPTION OF DRAWINGS

Other and further objects, features, and advantages of the invention will be more explicit from the following detailed description taken with reference to the drawings wherein:

FIG. 5 is a view showing the manner in which cross-section shapes with respect to abstracted models of twisting yarns are determined in step b1 in FIG. 4;

FIG. 6 is a view showing the manner in which the cross-section shapes of the twisting yarns are arranged around an arrangement reference point O in step b2 in FIG. 4;

FIG. 15 is a side view showing an example of the simulation result of an image of a twisted yarn according to the embodiment in FIG. 2.

BEST MODE FOR CARRYING OUT THE INVENTION

Figure 1:
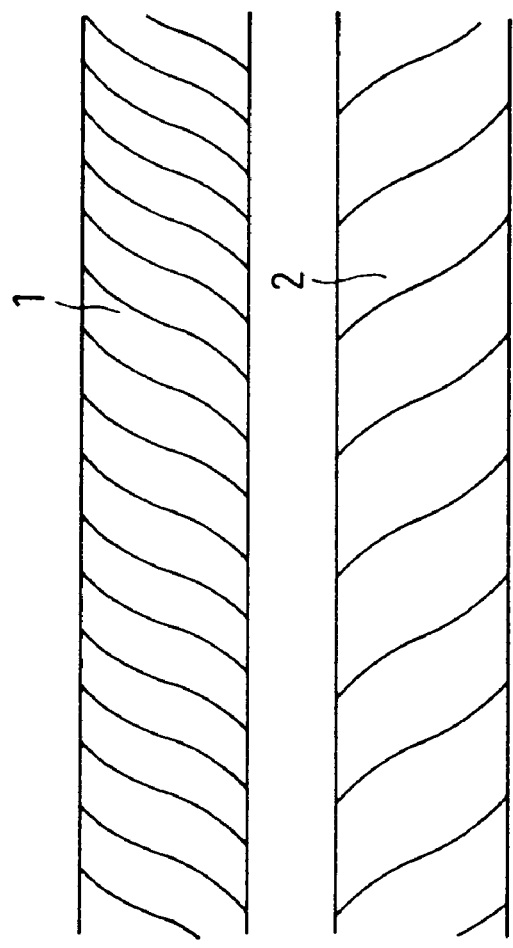
FIG. 1 is a view showing an outline of a method for simulating an image of a twisted yarn according to an embodiment of the invention, and shows a side view of two yarns 1 and 2 used for twisting, a cross-sectional view of an abstracted model 5 of a twisted yarn formed by twisting abstracted models 3 and 4 of yarns produced by abstracting the yarns 1 and 2, and a side view of a projected image 6 of the twisted yarn.

Now referring to the drawings, preferred embodiments of the invention are described below.

FIG. 1 shows a basic concept of simulating twisting of two yarns and forming an image of a twisted yarn as an embodiment of the invention. FIG. 1(a) shows a side view of two twisting yarns 1 and 2 used for twisting. FIG. 1(b) shows a cross-section shape of an abstracted model 5 of a twisted yarn formed by twisting abstracted models 3 and 4 of twisting yarns produced by abstracting the twisting yarns 1 and 2. FIG. 1(c) shows a projected image 6 of the twisted yarn. It should be noted that for yarns that are twisted to produce a twisted yarn, it is possible to use single fiber yarns such as monofilament as well as yarns produced by twisting fiber serving as material such as the twisting yarns 1 and 2.

The images of the two twisting yarns 1 and 2 as shown in FIG. 1(a) can be input by taking images of the actual twisting yarns 1 and 2 with a scanner or the like. Furthermore, the images can be created by computer graphics or the taken photographic image can be further edited. As shown in FIG. 1(b), the twisting yarns 1 and 2 are abstracted to be the abstracted models 3 and 4 of twisting yarns whose cross-sections are certain ellipses. In the case where the two twisting yarns 1 and 2 have an equal shape, the abstracted model 5 of a twisted yarn is obtained as a locus formed by rotating the cross-sections of the abstracted models 3 and 4 of the twisting yarns around a central axis 5a. The projected image 6 of the twisted yarn as shown in FIG. 1(c) is obtained, for example, as a state in which FIG. 1(b) is seen from the right side, and a portion on the left side of the abstracted models 3 and 4 of the two twisting yarns is hidden. Furthermore, since the abstracted models 3 and 4 of the twisting yarns are deformed in the form of spiral around the central axis 5a, the projected image 6 is deformed in the form of wave line. The projected image 6 of the twisted yarn is formed by reproducing the images of the twisting yarns 1 and 2 respectively on the portions of the projected image corresponding to the abstracted models 3 and 4 of the twisting yarns.

FIG. 1 shows a basic manner in which the projected image 6 of a yarn twisted by using only two of twisting yarns 1 and 2 that are equal to each other is obtained. In the invention, however, there is no limitation regarding the number of twisting yarns and it is also possible to apply twisting yarns that are not equal to each other.

Figure 2:
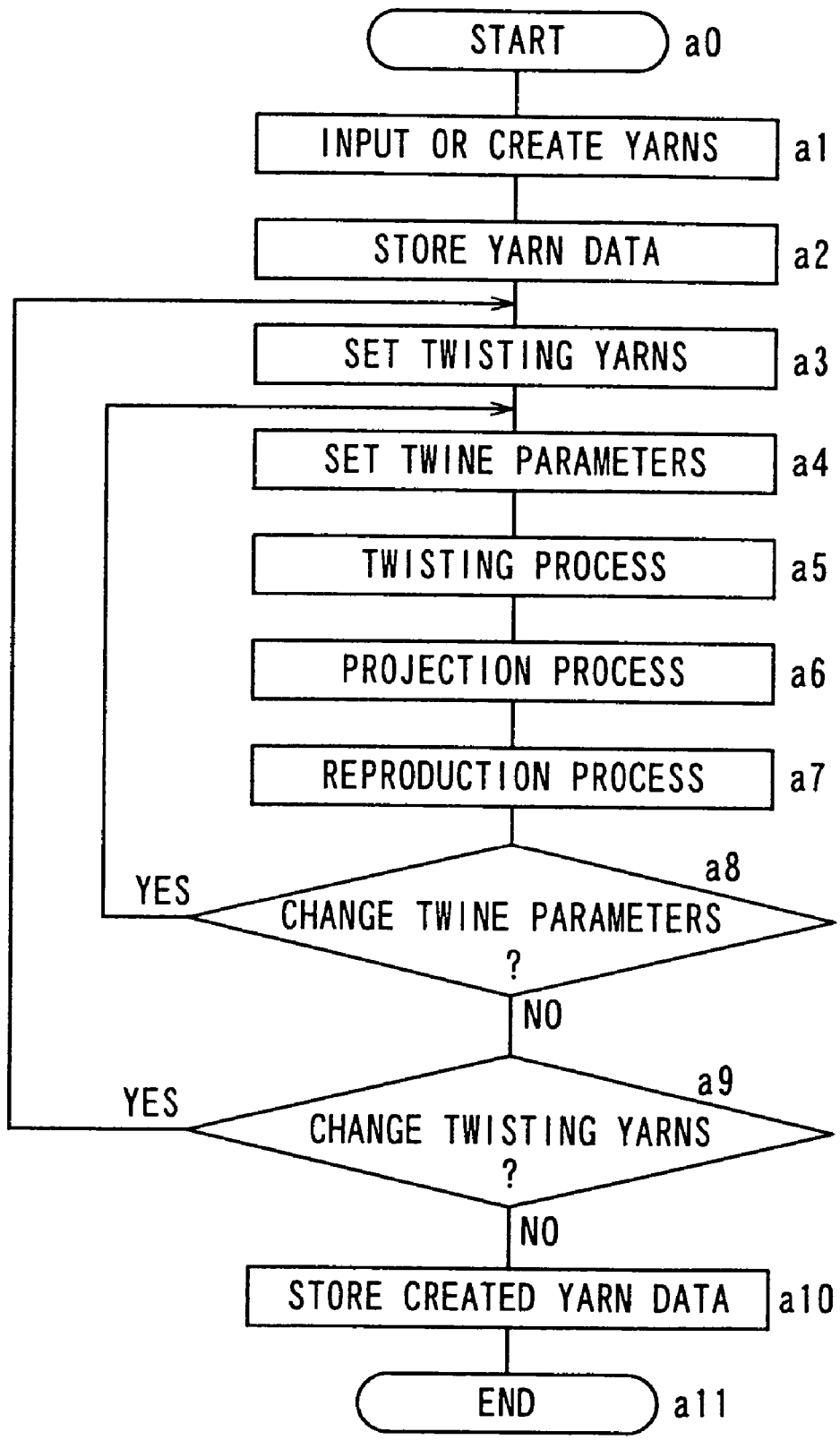
FIG. 2 is a flowchart showing a general procedure of executing a method for simulating an image of a twisted yarn as another embodiment of the invention.

FIG. 2 shows a general procedure of simulating an image of a twisted yarn as another embodiment of the invention. The procedure starts in step a0, and in step a1, images of twisting yarns are input or created in a similar manner as in FIG. 1(a). As described above, the images of the twisting yarns can be input with a scanner or the like and processed, or it is also possible to newly create the images as two-dimensional images with, for example, a yarn creation program and to express fuzz by utilizing a transparent component. The images of the twisting yarns are treated separately for a main frame portion on the inner circumferential side excluding fuzz and for the fuzz region on the outer circumferential side. When the images are input, parameters for determining the main frame portion and the fuzz region of the twisting yarns and other information such as definition are input or created. In step a2, the images, parameters and information that have been input or created in step a1 are stored as data for each twisting yarn. In steps al and a2, a larger number of twisting yarns than the number of twisting yarns actually used for twisting can be input or created.

In step a3, the twisting yarns are set so as to show which yarns are used as twisting yarns that are twisted to produce a twisted yarn. In step a4, twine parameters such as the number of yarns for twine, the direction of twine, the number of twisting per predetermined unit length, and rendering definition are set. Also, information that is to be used for various adjustments (described below) is set in advance. In step a5, a twisting process is performed in a similar manner as in FIG. 1(b). In step a6, a projection process is performed on an abstracted model of the twisted yarn in a similar manner as in FIG. 1(c). Instep a7, a reproduction process of reproducing the images of the twisting yarns onto the projected image is performed to display the simulation result of the image of the twisted yarn. In step a8, it is determined whether or not the twine parameters should be changed in light of the simulation result. In the case where the twine parameters are changed, the procedure returns to step a4. In the case where the twine parameters are not changed in step a8, it is determined whether or not the twisting yarns used for twisting should be changed in step a9. In the case where the twisting yarns are changed, the procedure returns to step a3. In the case where no change is made regarding the twisting yarns in step a9, the created yarn data of, for example, the twisted yarn is stored in step a10, and the procedure ends in step a11.

More specifically, this embodiment includes step a1 as an image input step in which images of a plurality of twisting yarns used for twisting are input in the forms of extended lines, step a2 as an abstracting step in which based on the images that have been input in the image input step, an abstracted model for each of the twisting yarns that extends in one direction and has a certain cross-section of a predetermined mathematizable shape is produced to abstract each of the yarns, and correspondence between the abstracted models and the images is set, step a5 as a twisting step in which the abstracted models of the plurality of twisting yarns that have been abstracted in the abstracting step are twisted according to a predetermined condition to produce an abstracted model of the twisting yarns twisted in a form extending along the central axis, step a6 as a projection step in which the abstracted model of the twisted yarn that has been produced in the twisting step is projected onto a plane that is in parallel with the central axis of the twisted yarn, and step a7 as an image reproduction step in which based on the correspondence that has been set in the abstracting step, the images of the twisting yarns are reproduced on the corresponding projected images of the abstracted models of the twisting yarns included in the abstracted model of the twisted yarn that has been projected onto the plane in the projection step.

It should be noted that yarn data stored in step a10 allows simulation of a state in which a knitting fabric is knitted, using a technology such as disclosed in Japanese Patent Application No. 2001-310559 (described above). More specifically, with the use of a conventional technique disclosed in WO9816823 or other documents, a three-dimensional model of a twisted yarn is produced, and by utilizing an image of the twisted yarn produced by reproducing an image of each twisting yarn on a projected image of an abstracted model of each of the twisting yarns included in a projected image of the abstracted model of the twisted yarn that has been projected on a plane in the image reproduction step, it is possible to simulate an image of a knitting fabric knitted by using the twisted yarn.

Figure 3:
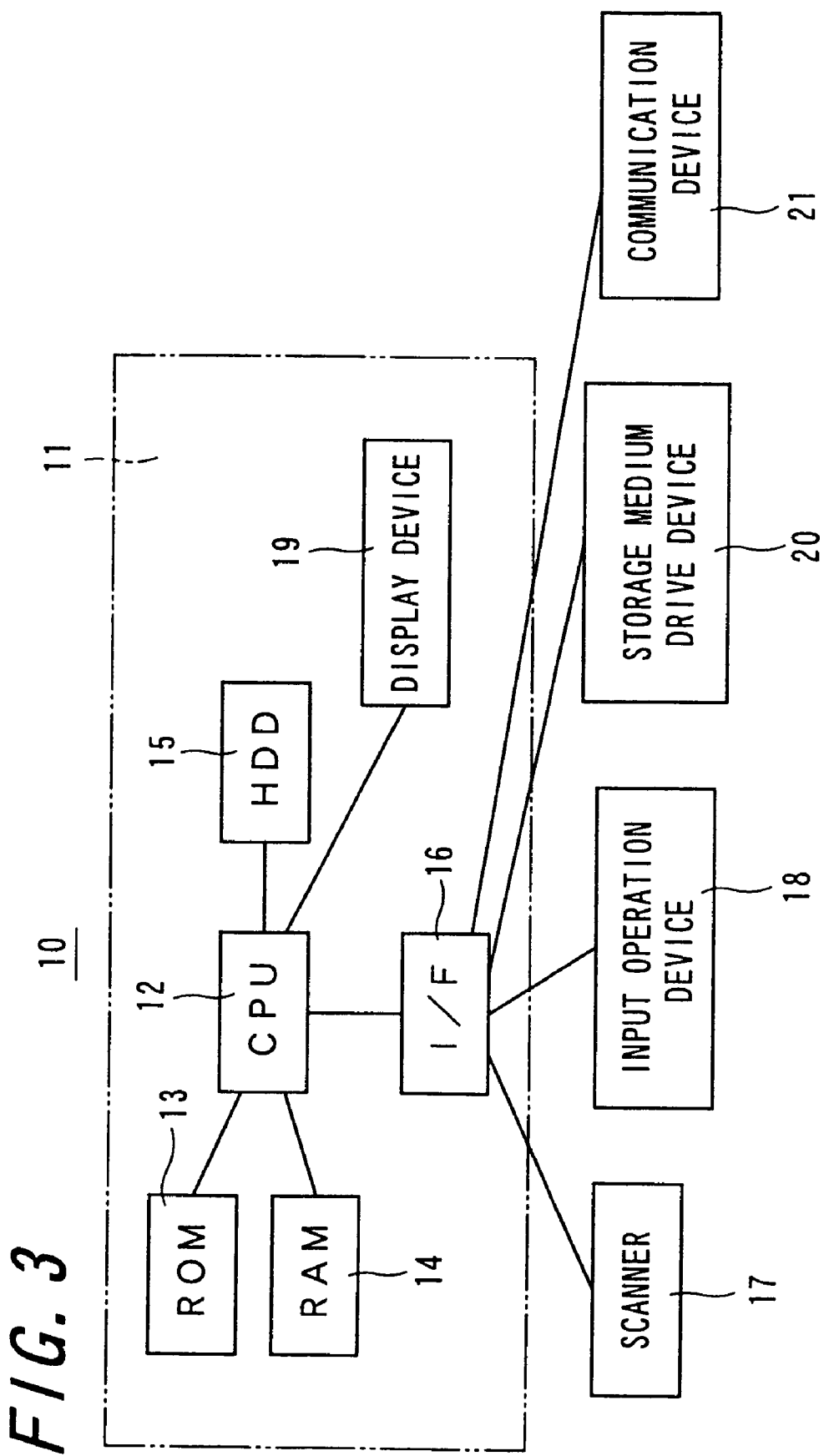
FIG. 3 is a block diagram showing an outlined electrical structure of an apparatus 10 for simulating an image of a twisted yarn, with which it is possible to execute the method for simulating an image of a twisted yarn according to the embodiment in FIG. 1 or 2.

FIG. 3 shows an outlined structure of an apparatus 10 for simulating an image of a twisted yarn, with which it is possible to execute the method for simulating an image of a twisted yarn according to the embodiment in FIG. 1 or 2. The steps in the above described procedure are realized when a CPU 12 contained in a computer 11 operates following programs stored in, for example, a ROM 13 or a RAM 14. The programs are stored in, for example, a hard disk device (hereinafter, abbreviated as "HDD") 15 in advance, and the CPU 12 operates by reading out the programs on the RAM 14 when necessary. Programs relating to, for example, basic operations are stored in the ROM 13 in advance.

In the programmed operation of the CPU 12, a two-dimensional image of a yarn is input using a scanner 17 connected via an interface (hereinafter, abbreviated as "I/F") 16 as means for inputting an image. Furthermore, also from an input operation device 18 such as a keyboard, a graphic tablet, and a mouse, input data and so forth can be input to the CPU 12 via the I/F 16. A simulation image of a twisted yarn and an input image of a yarn that are produced by the programmed operation of the CPU 12 are displayed by a display device 19 such as a cathode ray tube (CRT) and a liquid crystal display (LCD). The program executed by the CPU 12 also can be stored onto a storage medium that is removable from a storage medium drive device 20, such as a CD (compact disk)-ROM and other optical disks and a flexible disk and other magnetic storage media, and can be read on the HDD 15 or the RAM 14. It is also possible to use the program transferred from an information network such as a LAN (local area network) or the Internet via a communication device 21 such as a modem or a router.

Figure 4:
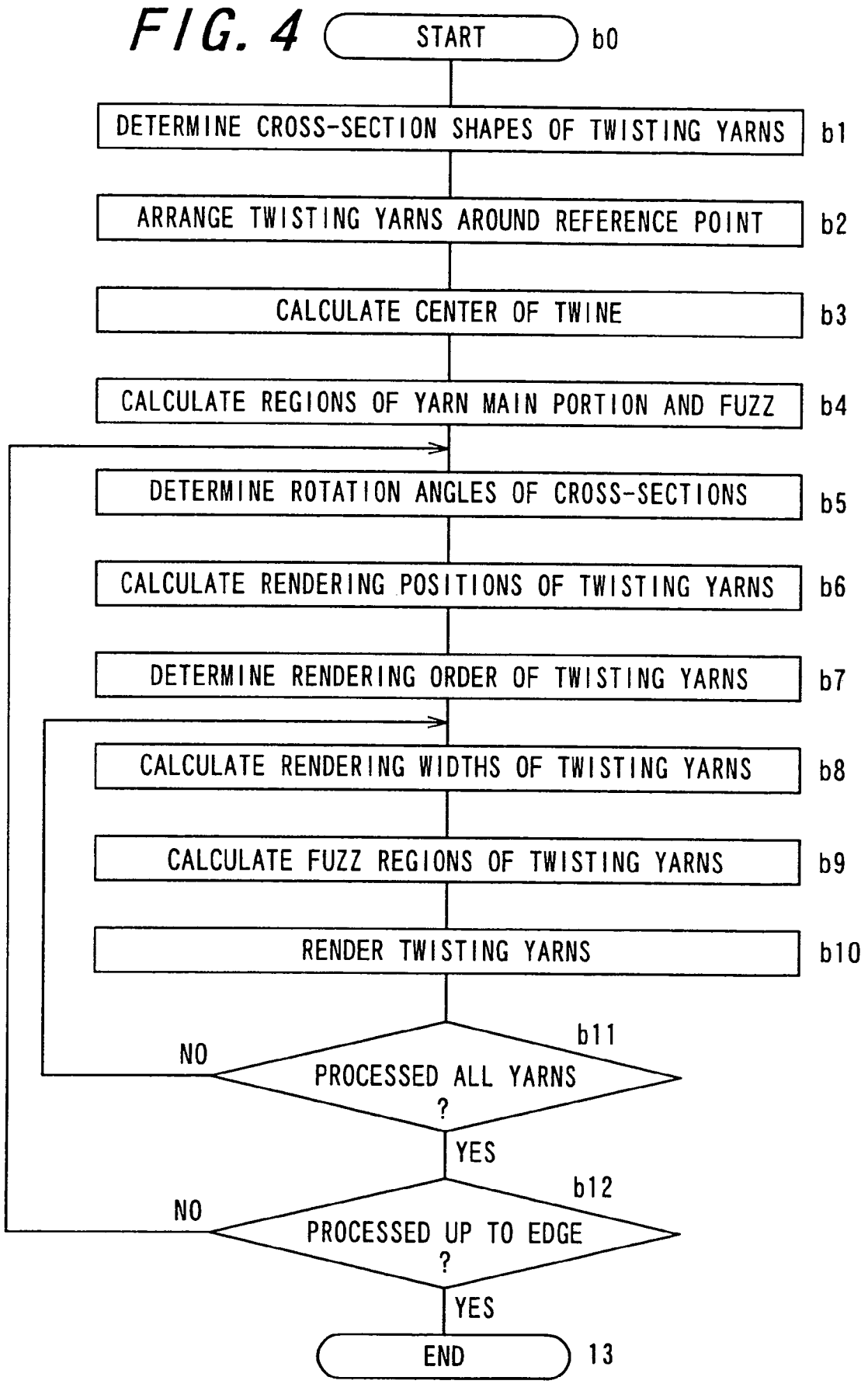
FIG. 4 is a flowchart showing the procedure with respect to a process of rendering twine in which twisting in step a5, projection in step a6, and image reproduction in a7 in the embodiment in FIG. 2 are combined.

FIG. 4 shows the procedure with respect to a process of rendering twine in which twisting in step a5, projection in step a6, and image reproduction in a7 in the embodiment in FIG. 2 are combined. The procedure starts in step b0, and in step b1, the cross-section shapes of the abstracted models of the twisting yarns are determined as round shapes. In step b2, an arrangement reference point is set and the cross-section shapes of the abstracted models of the twisting yarns are arranged around the arrangement reference point and flattened. In step b3, the center of the twine is calculated. In step b4, the main frame portion and the fuzz region of the twisting yarns are calculated. The procedure of steps b1 to b4 corresponds to the twisting shown in step a5 in FIG. 2. Also, it is possible to flatten the cross-section shapes at the stage of determining the cross-section shapes of the abstracted models.

In step b5 in FIG. 4, the rotation angles of the cross-sections around the center of the twine are determined based on the twine parameters. In step b6, with respect to the abstracted models of the twisting yarns, the rendering positions along the central axis obtained by extending the center of the twine in one direction are calculated. In step b7, the rendering order of the abstracted models of the twisting yarns is determined. The procedure of steps b5 to b7 corresponds to the projection shown in step a6 in FIG. 2.

In step b8 in FIG. 4, with respect to the projected images of the abstracted models of the twisting yarns, the rendering widths are calculated. In step b9, with respect to the projected images of the abstracted models of the twisting yarns, the fuzz regions are calculated. In step b10, reproduction is performed in which the images of the twisting yarns are applied to the projected images of the twisting yarns. In step b11, it is determined whether or not all of the yarns set as the twisting yarns in step a3 in FIG. 2 have been processed. In the case where all of the yarns have not been processed yet, the procedure returns to step b8. The procedure of steps b8 to b11 corresponds to the image reproduction shown in step a7 in FIG. 2. In the case where it is determined that all of the yarns have been processed in step b11, in step b12, it is determined whether or not a portion up to the edge of the twisted yarn has been processed along the central axis, and the procedure returns to step b5 when the process has not been completed up to the edge. When it is determined that the process has been completed up to the edge in step b12, the procedure ends in step b13.

FIG. 5 shows the manner in which, with respect to the abstracted models of the twisting yarns, the arrangement of the cross-section shapes are determined and the cross-section shapes are flattened in steps b1 and b2 in FIG. 4. In the case where three twisting yarns are used, the diameters of the round cross-sections of the twisting yarns are taken as W1, W2 and W3, and then the diameters in the radial directions toward the arrangement reference point O are contracted to be zx1, zx2 and zx3 with taking the directions as x-directions that are the longitudinal directions. The diameters in the lateral directions as circumferential directions perpendicular to the x-directions are magnified to be zy1, zy2 and zy3 with taking the directions as y-directions. A circumference around the arrangement reference point o is divided into L1, L2 and L3 based on the ratios of the square roots of the diameters W1, W2 and W3 of the twisting yarns, and in accordance with the ratios, scaling in the longitudinal and lateral directions is calculated. More specifically, the cross-section shapes of the abstracted models of the twisting yarns are ellipses arranged around the arrangement reference point O, and are flattened in such a manner that the lengths of the minor axes are $zx1$, $zx2$ and $zx3$ times, and the lengths of the major axes are $zy1$, $zy2$ and $zy3$ times of each diameter W1, W2 and W3, respectively, of the round cross-sections.

In this embodiment, the cross-section shapes of the abstracted models of the twisting yarns are flattened based on the thicknesses thereof. First, the arrangement reference point O is set, and the cross-section shapes of the abstracted models of the twisting yarns are arranged around the arrangement reference point O. The cross-section shapes are abstracted to be round, and are flattened to be elliptical in accordance with the number and the thickness of the twisting yarns. For example, in the case where n twisting yarns are used for twisting, when the diameters of the round cross-sections of the twisting yarns are taken as W1, ..., Wn, a proportion $\kappa m$ at which a diameter Wm of the m-th twisting yarn ($1 \leq m \leq n$) occupies around the arrangement reference point O is set to be proportional to the ratio of the square root of the diameter Wm, based on Equation (1) below.

$$\kappa m = \frac{\sqrt{Wm}}{\sqrt{W1} + \ldots + \sqrt{Wn}} \quad \text{Equation (1)}$$

It should be noted that when the ratio $\kappa m$ of the square root of the diameter Wm satisfies $\kappa m > 0.5$, the ratio $\kappa m$ is corrected to satisfy $\kappa m = 0.5$. This is because even when the ratio of the diameter of one twisting yarn occupies a half or more of the entire portion, it is impossible to arrange an ellipse occupying more than a half of the region around the arrangement reference point O on the plane, and thus the ratio $\kappa m$ is corrected to be 0.5. Furthermore, when the ratio satisfies $\kappa m < 0.2$, the ratio is uniformly corrected to satisfy $\kappa m = 0.2$. This is because in a small region, flattening can be ignored. Accordingly, when at least two twisting yarns are used and have the same width, it is possible to flatten and process the twisting yarns up to five.

The scaling is set based on a scale factor zm satisfying Equation (2) below.

$$zm = \frac{\alpha \times (\kappa m - 0.2)}{0.5 - 0.2} \quad \text{Equation (2)}$$

Herein, it is assumed that α is a constant set to satisfy, for example, α=0.1. This value of α can be changed when necessary. By using the scale factor zm in Equation (2), scale factors in the longitudinal and lateral directions are determined with Equations (3) and (4) below.

$$zxm = 1.0 - zm \quad \text{Equation (3)}$$

$$zym = 1.0 + zm \quad \text{Equation (4)}$$

In FIG. 5, since the diameter W1 of the cross-section shape with the center C1 is comparatively small, the cross-section shape is flattened less. The cross-section shape with the center C2 is flattened.

FIG. 6 shows the manner in which the cross-section shapes of the twisting yarns are arranged around the arrangement reference point O. The region around the arrangement reference point O serving as the center of the arrangement is divided in the above-described proportion of L1, L2 and L3. FIG. 6(a) shows a case of three twisting yarns and FIG. 6(b) shows a case of two twisting yarns. As shown in FIG. 6(a), the central positions of the twisting yarns are taken as C1, C2 and C3, respectively. The distances from the arrangement reference point O to the centers C1, C2 and C3 are taken as r1, r2 and r3, respectively. The cross-section shapes of the twisting yarns are in contact with boundary lines passing through the arrangement reference point O. When the angles formed between the boundary lines passing through the arrangement reference point O and lines connecting the arrangement reference point O and the centers C1, C2 and C3 respectively are taken as θ1, θ2 and θ3, θm is determined based on Equation (5) below (when $1 \leq m \leq 3$).

$$\theta m = \frac{360 \times \kappa m}{2} \quad \text{Equation (5)}$$

Thus, a distance rm is determined based on Equation (6) below.

$$rm = \sqrt{\left[\frac{Wm}{2} \times zxm \times \sin(\theta m)\right]^2 + \left[\frac{Wm}{2} \times zym \times \cos(\theta m)\right]^2} \quad \text{Equation (6)}$$

Accordingly, the central coordinate of Cm is determined based on Equations (7) and (8) below.

$$cxm = rm \times \cos(\alpha m) \quad \text{Equation (7)}$$

$$cym = rm \times \sin(\alpha m) \quad \text{Equation (8)}$$

Herein, FIG. 6(a) shows that α1=0, α2=θ1+θ2, α3=α2+θ2+θ3.

More specifically, in the step of determining the cross-section shapes such as shown in step b1 in FIG. 4, the cross-section shapes of the plurality of twisting yarns that have been input in the above-described image input step are abstracted as round shapes to produce abstracted models of the twisting yarns.

Furthermore, in the step of arranging the twisting yarns around the arrangement reference point O such as shown in step b2, the cross-sectional region around the arrangement reference point O is divided in accordance with the ratio of the square root of the diameter Wm obtained when the cross-sections of the abstracted models of the twisting yarns are abstracted as round shapes, and the cross-section shapes of the abstracted models of the twisting yarns are arranged in such a manner that the cross-section shapes of the adjacent twisting yarns are in contact with each other on a boundary line between the divided regions. At the time of arrangement, the cross-section shapes are flattened as well. It should be noted that a flattening proportion of the cross-section shapes of the abstracted models may vary based on a material of the twisting yarns.

FIG. 6(b) shows a state in which, in the case where two twisting yarns are used, one diameter is larger than the other, and thus the ratio of the diameter is larger than half, the twisting yarn is adjusted so as to occupy a half of the region around the arrangement reference point O. In other words, in the case of the two twisting yarns, L1=L2 is satisfied. In this manner, in the step of arranging the cross-sections, when the ratio of the square root of the abstracted model of one twisting yarn occupies a half or more of the entire portion, adjustment is performed so that the abstracted model of the twisting yarn occupies only a half of the cross-sectional region around the arrangement reference point O.

Figure 7:
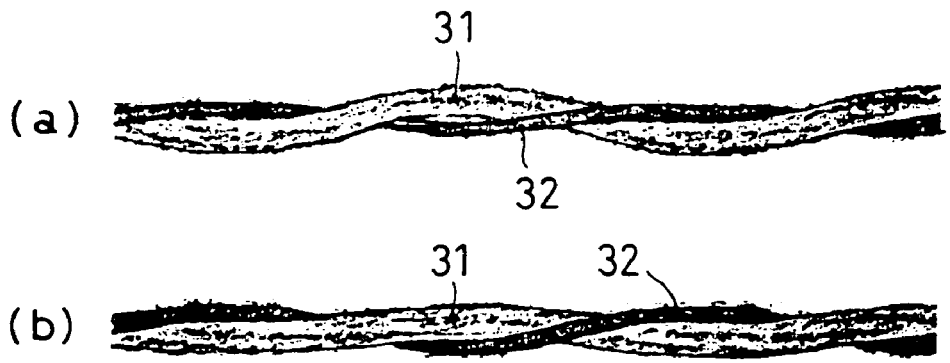
FIG. 7 is a side view showing the effect of displacing the center of twine when twisting yarns whose thicknesses are different from each other are twisted as shown in FIG. 6(b)

FIG. 7 shows the effect of displacing the center of twine when twisting yarns whose thicknesses are different from each other are twisted as shown in FIG. 6(b). FIG. 7(a) shows a case in which the arrangement reference point O is the central axis of a twisted yarn, and FIG. 7(b) shows a case in which the central axis of the twine is set at a position apart from the arrangement reference point O. In FIG. 7(a), a thick twisting yarn bulges outward more significantly, and a thin twisting yarn 32 looks undulating because the thin twisting yarn 32 rotates at a position near the center. In FIG. 7(b), undulation is reduced by setting the central axis serving as the rotation center of the twine at a position that is obtained with the weighted average of the distances from the arrangement reference point to the center positions of all of the twisting yarns, and taking the length of the diameter of each twisting yarn as the weight. Conversely, by arbitrarily displacing the central position, undulation caused by a difference between tensile forces for the twisting yarns in twisting can be expressed to some extent.

When SumW=ΣWm and SumC=Σ(Cm×Wm), a position R of the central axis based on the weighted average for the purpose of reducing undulation can be expressed by Equation (9) below, using the arrangement reference point O as the reference.

$$R = \frac{SumC}{SumW} \qquad \text{Equation (9)}$$

Figure 8:
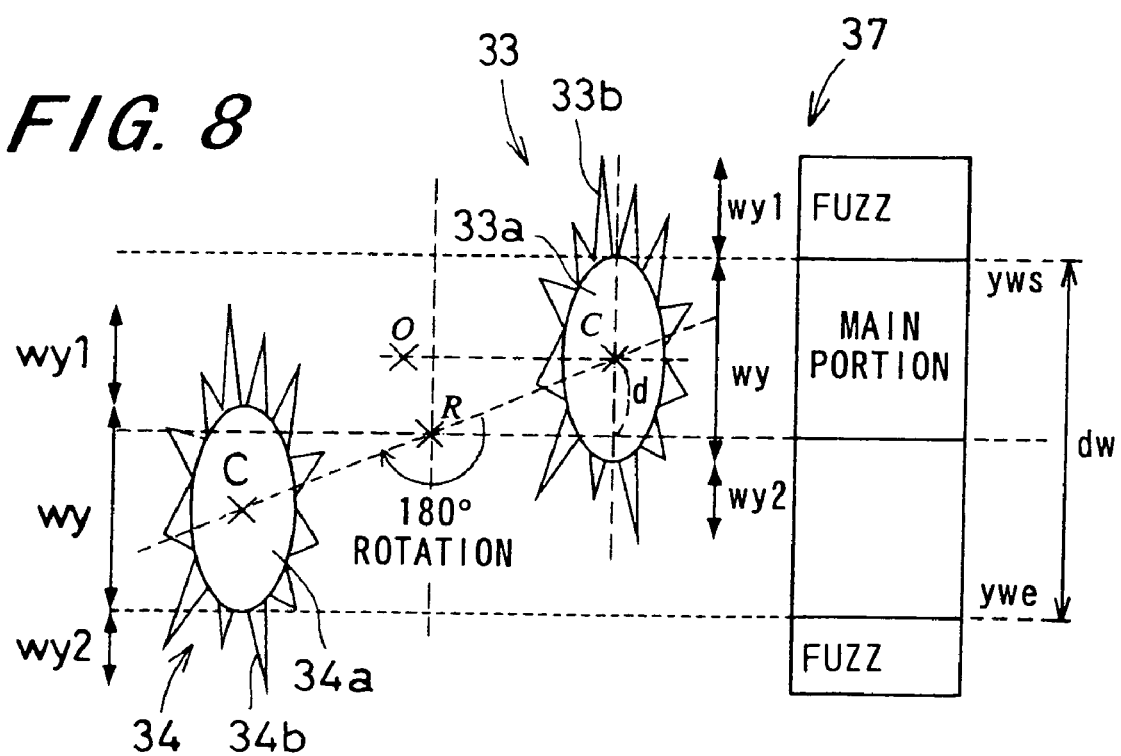
FIG. 8 is a view showing the manner in which the size of an image and the position of a yarn main portion with respect to a fuzzy twisting yarn are calculated.
Figure 9:
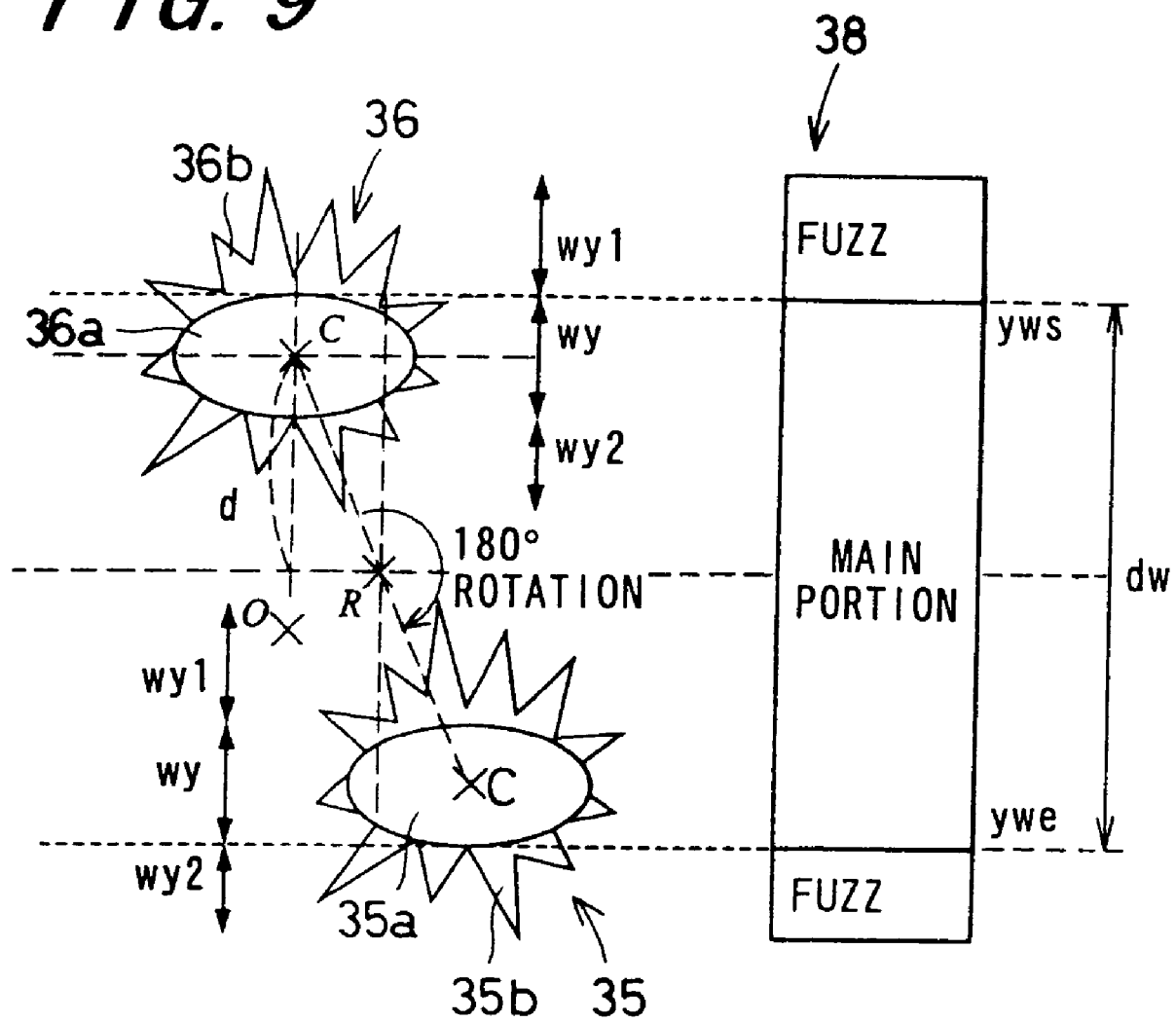
FIG. 9 is a view showing the manner in which the size of ah image and the position of a yarn main portion with respect to a fuzzy twisting yarn are calculated.

FIGS. 8 and 9 show the manner in which with respect to a fuzzy twisting yarn, an abstracted model of the twisting yarn is produced separately for a fuzz portion on the outer circumferential side and for a yarn main portion on the inner circumferential side excluding the fuzz, and of calculating the size of an image and the position of the yarn main portion for rendering the portions. FIG. 8 shows a state in which, when an abstracted model of one twisting yarn is projected in the longitudinal direction of the figure, the minor axes of cross-section shapes 33 and 34 are in parallel with the projection direction. When an angle formed between the projection direction and a line passing from the arrangement reference point O to each of the centers C of the cross-section shapes 33 and 34 is taken as a rotation angle, the rotation angle of the cross-section shape 33 is 0 and that of the cross-section shape 34 is 180°. In these cross-section shapes 33 and 34, the major axes are perpendicular to the projection direction. FIG. 9 show a state in which the major axes of cross-section shapes 35 and 36 are in parallel with the projection direction. As for the rotation angle with respect to a line passing from the arrangement reference point O to each of the centers C of the cross-section shapes, the rotation angle of the cross-section shape 35 is 90°, and that of the cross-section shape 36 is 270°.

Hereinafter, the projection direction is taken as x-direction, which is toward from left to right of the sheet for the drawing, and the direction from bottom to top, which is perpendicular to the projection direction, is taken as y-direction.

In step b1 in FIG. 4, which is the process of determining the cross-section shapes 33, 34, 35 and 36 of the abstracted models of the twisting yarns, yarn main portions 33a, 34a, 35a and 36a on the inner circumferential side and fuzz portions 33b, 34b, 35b and 36b on the outer circumferential side are treated separately. In the procedure from the process of arranging the twisting yarns around the arrangement reference point O in step b2 to the process of calculating the rendering widths of the twisting yarns in step b8, all steps except for step b4 are performed based on the yarn main portions 33a, 34a, 35a and 36a. In step b4, the width wy of the regions of the yarn main portions 33a, 34a, 35a and 36a and the widths wy1 and wy2 of the regions of the fuzz portions 33b, 34b, 35b and 36b of the twisting yarns are calculated.

In FIGS. 8 and 9, projected image ranges. 37 and 38 are also shown. The plane on which the images are projected is in parallel with the central axis passing through the rotation center R, and the intersecting line with the sheet for the drawing is a line extending in the longitudinal direction. As fuzz, wy1 and wy2 are added to the upper side and the lower side of the projected image ranges 37 and 38.

In the projected image ranges 37 and 38, a range from yws to ywe is a width dw of the yarn main portions 33a, 34a, 35a and 36a. When a distance from the line passing through the rotation center R in the projection direction to the centers C of the cross-section shapes 33, 34, 35 and 36 is taken as d, the width dw can be calculated based on Equation (10) below.

$$dw = 2 \times \left(\frac{1}{2} \times wy + d\right) = wy + 2 \times d \qquad \text{Equation (10)}$$

A larger one of the values of the width dw calculated at the rotation angles 0/180° and 90/270° is taken to be the value of the width of a yarn main portion at any rotation angle. The entire width of the twisting yarn is one obtained by adding the width of the yarn main portion and the width of the fuzz.

In step b5 in FIG. 4, when the process is performed along the central axis line of the twisted yarn, a rotation angle β of the cross-section is determined based on the twine parameters that have been set as the number of twisting per unit length. In step b6, the rendering positions of the twisting yarns are calculated after calculating the central positions C. When the rotation angle β is 0, the position coordinate of the center C of the cross-section shape with relative to the rotation center R is expressed based on Equation (11) below as the two-dimensional coordinate (cx, cy) in which the projection direction is the x-direction as described above, when the arrangement reference point O is the origin, the coordinate of the center C is taken as C (x, y), and the coordinate of the rotation center R is taken as R(x, y).

$$(cx, xy)=C(x, y)-R(x, y) \qquad \text{Equation (11)}$$

When the x,y-coordinate of the center C at the rotation angle β is taken as P(x) and P(y), the x,y-coordinate can be calculated based on Equations (12) and (13) below.

$$P(x)=cx \times \cos(\beta)-cy \times \sin(\beta) \qquad \text{Equation (12)}$$

$$P(y)=cx \times \sin(\beta)+cy \times \cos(\beta) \qquad \text{Equation (13)}$$

In step b7, which is the process of determining the rendering order of the twisting yarns, the order is determined so that the twisting yarns are rendered in a sequential manner from a twisting yarn having a smaller P(x), which is the x-component, of the position coordinates of the centers of the cross-section shapes.

Figure 10:
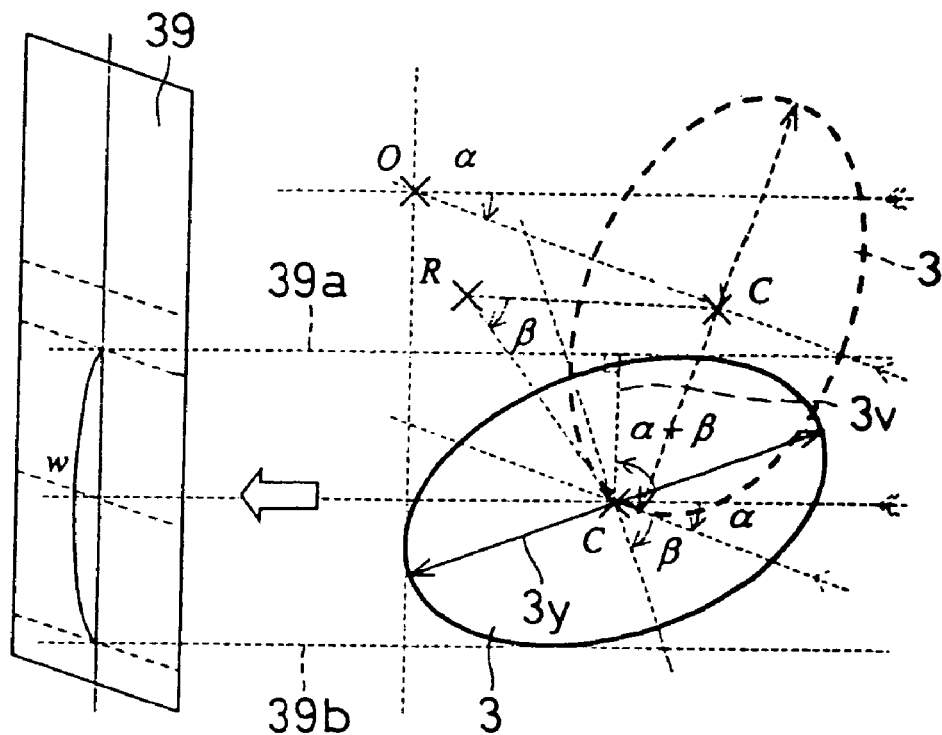
FIG. 10 is a view showing the manner in which a rendering width w is calculated in step b8 in FIG. 4.

FIG. 10 shows the manner in which with respect to the cross-section shape of the abstracted model 3 of one twisting yarn, a rendering width w is calculated in step b8, when the rotation angle determined in step b5 in FIG. 4 is taken as In the abstracted model 3 of the twisting yarn, the broken line shows a state in which the rotation angle β is 0, and the twisting yarn is arranged at a position where the center C of the cross-section shape forms an angle of α around the arrangement reference point O. As shown by the solid line, when the twisting yarn is rotated by the angle β around the rotation center R, the angle formed by a major axis 3*y* of the cross-section shape and a perpendicular line 3*v* to a tangent line 39*a* extending from the center C of the ellipse that is the cross-section shape to a plane 39 in the projection direction is α+β. The rendering width w on the plane 39 on which the twisting yarn is projected can be calculated as a gap between the tangent lines 39*a* and 39*b* that touch the top and bottom points of the ellipse that is the cross-section shape.

Figure 11:
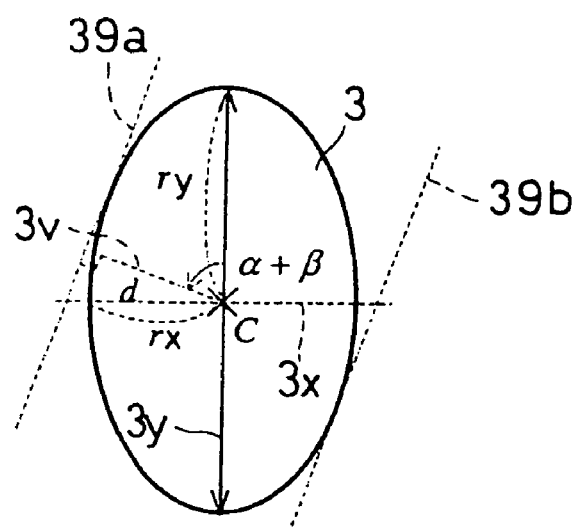
FIG. 11 is a view showing an ellipse shown in FIG. 10, taking the minor axis thereof as x-axis and the major axis as y-axis.

FIG. 11 shows the ellipse that is the cross-section shape of the abstracted model 3 of the twisting yarn shown in FIG. 10, taking the minor axis 3*x* as x-axis and the major axis 3*y* as y-axis. The equation of the perpendicular line 3*v* from the center C to the tangent line 39*a* can be expressed by Equation (14) below.

$$y = a \times x \qquad \text{Equation (14)}$$

It should be noted that $a=\tan(\alpha+\beta)$. Accordingly, the equations of the tangent lines 39*a* and 39*b*, which are lines touching the ellipse, can be expressed by Equation (15) below.

$$y = -\frac{1}{a} \times x \pm \sqrt{rx^2 \times \left(-\frac{1}{a}\right)^2 + ry^2} \qquad \text{Equation (15)}$$

A distance d can be expressed by Equation (16) below.

$$d = \sqrt{dx^2 + (a \times dx)^2} \qquad \text{Equation (16)}$$

$$\text{where } dx = \frac{\sqrt{rx^2 \times \left(-\frac{1}{a}\right)^2 + ry^2}}{a + \frac{1}{a}}$$

Since the tangent lines 39*a* and 39*b* are at vertically symmetrical positions, the width w of the twisting yarn that is horizontally projected can be calculated by doubling the distance d. In other words, w=2×d.

Figure 12:
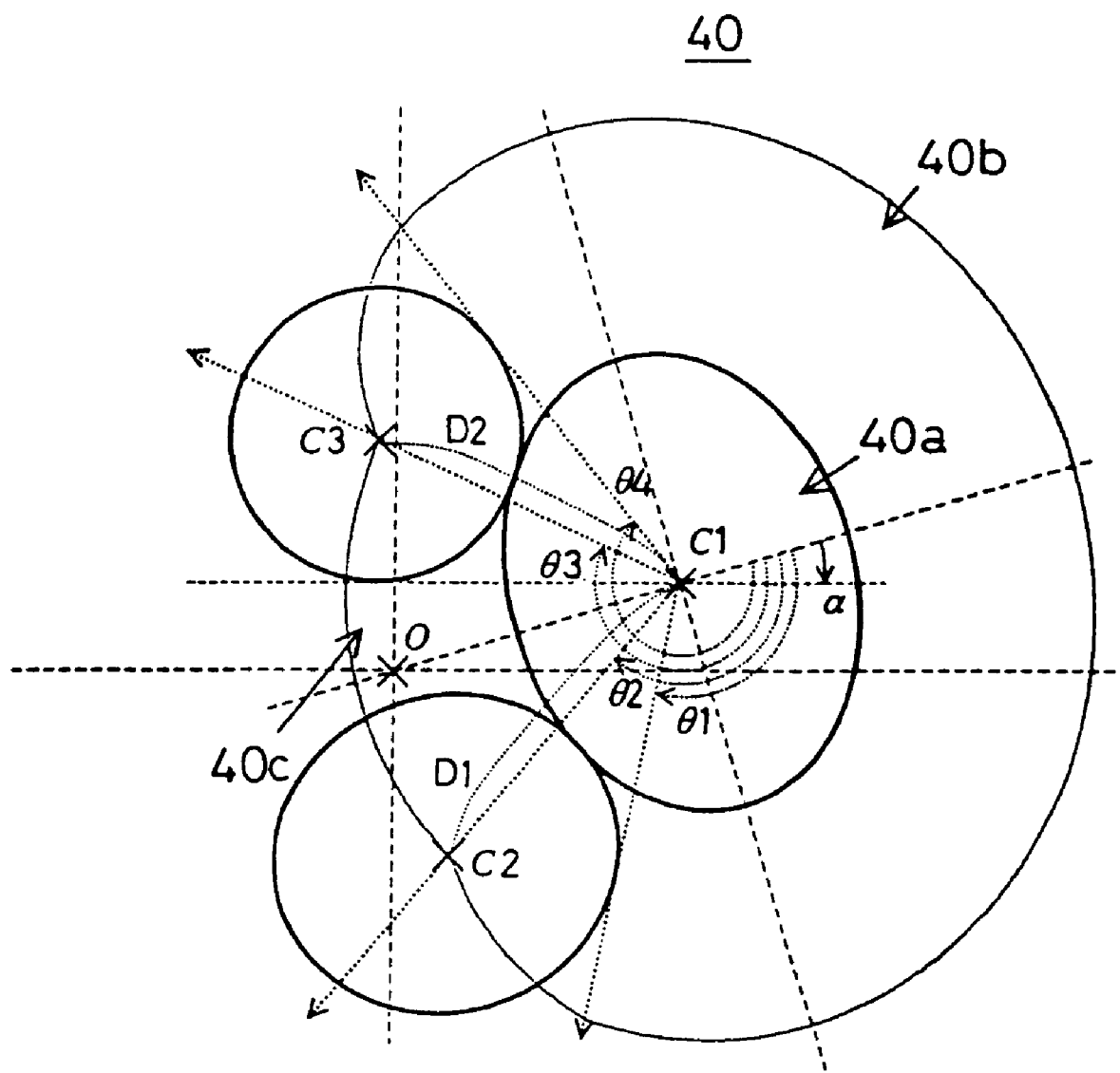
FIG. 12 is a view showing the manner in which a fuzz region of the twisting yarn is calculated in step b9 in FIG. 4.

FIG. 12 shows the manner in which the fuzz region of the twisting yarn is calculated in step b9 in FIG. 4. As described above, with respect to a yarn image 40 of a fuzzy twisting yarn, when arranging the cross-section shape of the abstracted model, a yarn main portion 40*a* is arranged and a region of fuzz 40*b* is added on the outer circumferential side thereof. In a region 40*c* in which there exist twisting yarns adjacent to the yarn main portion 40*a*, the width of the fuzz 40*b* is set not so as to exceed the centers of the adjacent twisting yarns. In the case where the twisting yarn with the center C1 has fuzz 40*b* and is adjacent to each of the twisting yarns with the centers C2 and C3, the following angles θ1, θ2, θ3 and θ4 are calculated. Herein, θ1 is formed in the direction of the left tangent line, when viewed in the direction from the center C1 to the center C2, of the tangent lines of the ellipse with the center C2. θ2 is formed in the direction of the center C2. θ3 is formed in the direction of the center C3. θ4 is formed in the direction of the right tangent line, when viewed in the direction from the center C1 to the center C3, of the tangent lines of the ellipse with the center C3. θ1 to θ4 are set based on the line passing from the arrangement reference point O to the center position C1 of the twisting yarn. The angle formed by this line with the reference direction, which is the x-direction, is taken as α.

The region of fuzz in the yarn image 40 is limited within a length λlim as shown below in accordance with the range of the angles θ around the center C1. However, since the yarn main portion 40*a* is included in the inner portion, the net region of fuzz is the region that is limited within the length λlim and excludes the yarn main portion 40*a* in the inner portion. Herein, λ is the width of the twisting yarn when there is no limitation, and D1 and D2 are distances from the center C1 to the centers C2 and C3. More specifically, the length from the center C1 of the twisting yarn to the edge of the fuzz is limited within interpolated values between λ and D1 when θ1<Θ≦θ2, between D1 and D2 when θ2<θ<θ3, and between D2 and λ when θ3 ≦<θ<θ4.

In the case where the density of the fuzz is high, the fuzz that cannot be accommodated within a gap with the adjacent twisting yarn might stick out, it is sometimes better to ease this limitation. The limitation of the region of fuzz can be adjusted in accordance with the density of the fuzz.

Figure 13:
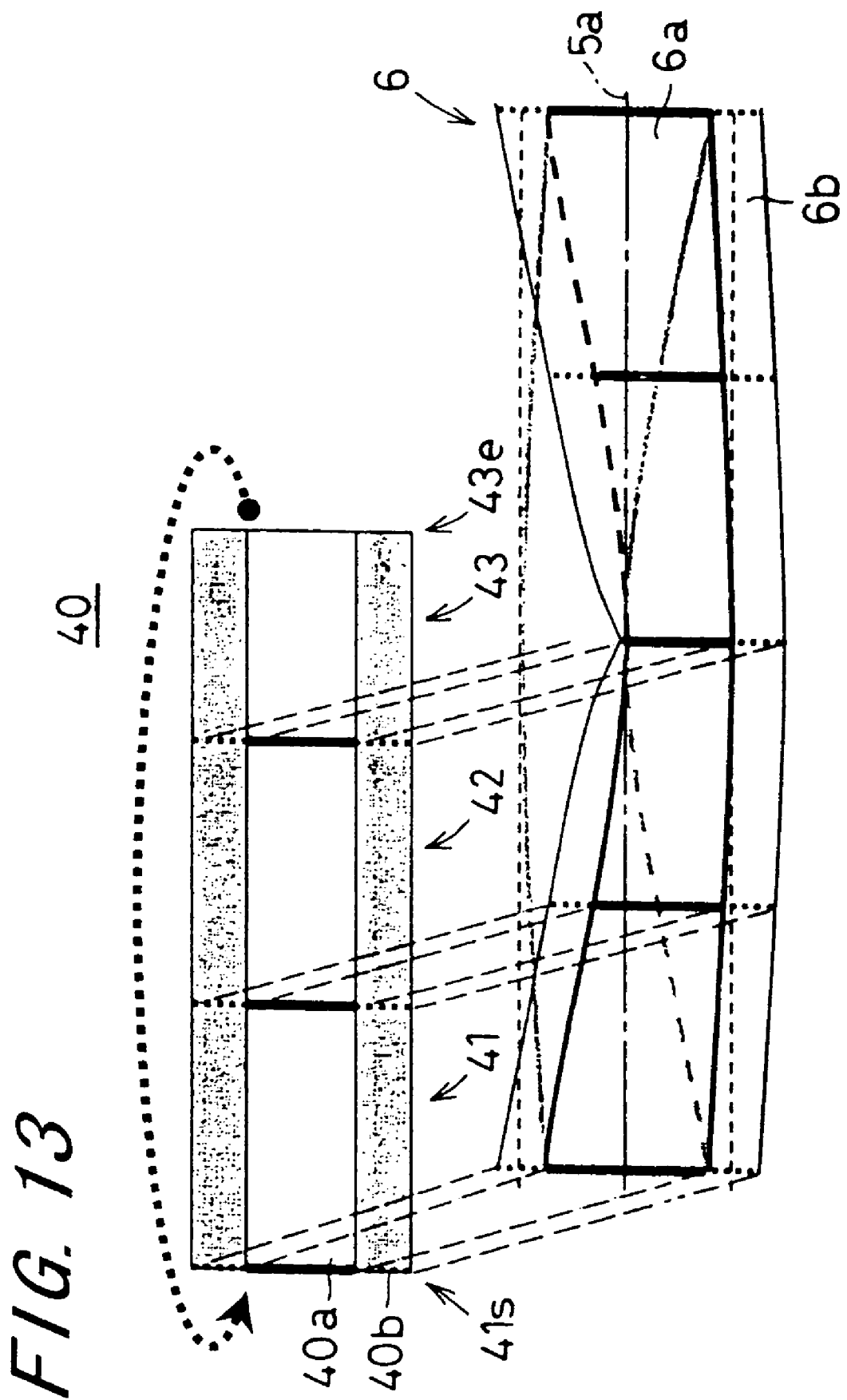
FIG. 13 is a side view showing the manner in which the fuzzy twisting yarn is rendered in step b10 in FIG. 4.

FIG. 13 shows the manner in which the twisting yarn is rendered in step b10 in FIG. 4, by reproducing the yarn image 40 that has been input as in FIG. 1(*a*) separately for the yarn main portion 40*a* and for the fuzz 40*b* on the projected image 6 of the twisted yarn that has been horizontally projected. In the step of rendering twine, a process is performed for each predetermined length along the central axis 5*a*. For convenience, it is assumed that sections 41, 42 and 43 correspond to this predetermined length. In an actual process, it is natural that shorter sections are set. The yarn main portion 40*a* of the yarn image 40 is reproduced in a sequential manner for each of the sections 41, 42 and 43 on the portion of a yarn main portion projected image 6*a* of the corresponding twisting yarn on the projected image 6 of the twisted yarn. Since the yarn main portion projected image 6*a* of the twisting yarn corresponds to the abstracted model whose cross-section is flattened, the width is changed. The fuzz 40*b* of the yarn image 40 is reproduced on a fuzz projected image 6*b* in a similar manner. However, the portion of the fuzz projected image 6*b* is limited based on the relation with the adjacent twisting yarns as shown in FIG. 12. After reproduction is performed up to the ending edge 43*e* of the section 43, reproduction is then repeated from the starting edge 41*s* of the section 41. By repeating reproduction in this manner from one edge to the other edge of a section that is used, it is possible to simulate a twisted yarn that is longer than the yarn image 40.

In the case where the shape of, for example, the fuzz 40*b* is changed significantly between the starting edge 41*s* and the ending edge 43*e* of the yarn image 40, the form sometimes becomes unnatural when the first section 41 continues after the last section 43. In such a case, it is not always necessary to use the entire length of the yarn image 40, and a portion that is suitable for continuation can be used. An image process can be performed in such a manner that the side of the starting edge 41*s* and the side of the ending edge 43*e* are superimposed and the degree of darkness is gradually changed lower on one side and higher on the other side, so that transition can be achieved.

Figure 14:
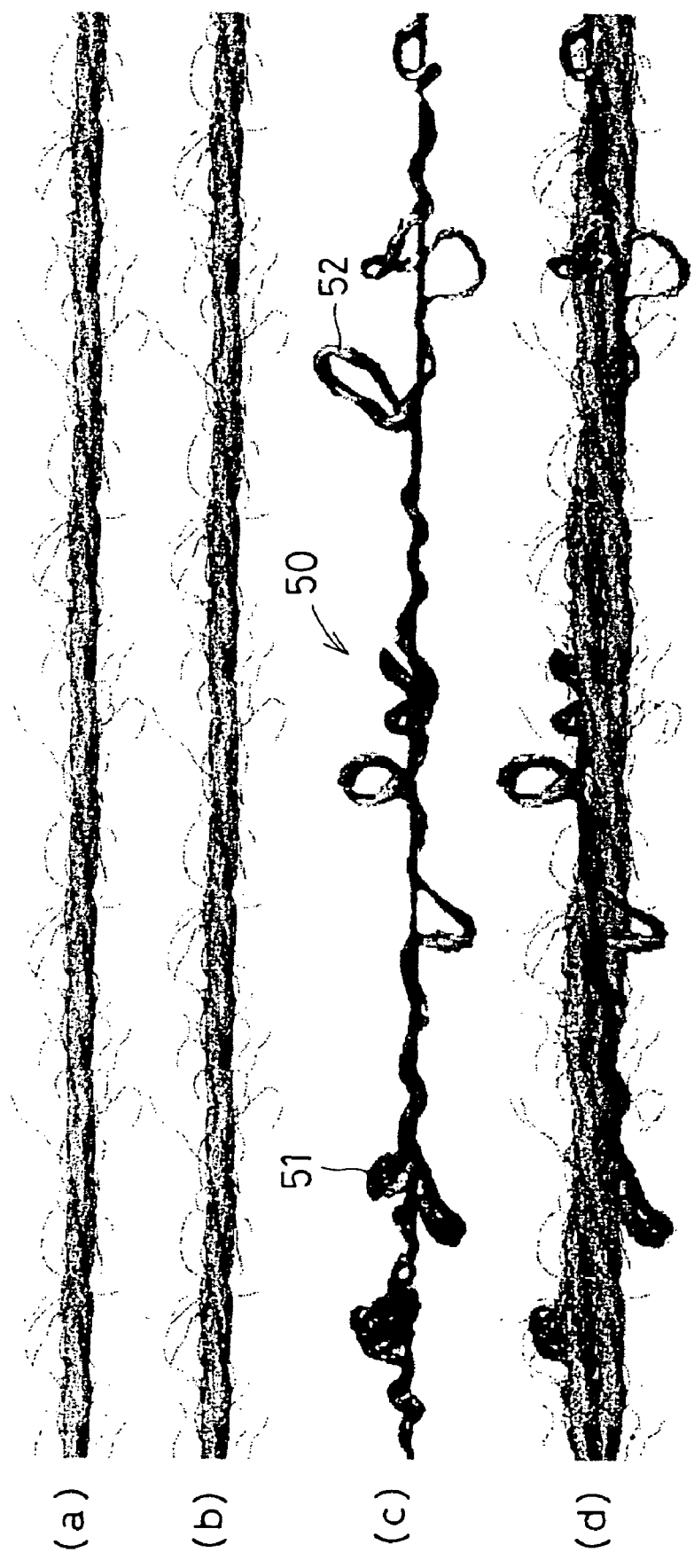
FIG. 14 is a side view showing an example of the simulation result of an image of a twisted yarn according to the embodiment in FIG. 2.

FIGS. 14 and 15 show examples of the simulation result of an image of a twisted yarn according to this embodiment. In FIG. 14, a simulation is performed in which three twisting yarns shown in FIGS. 14(*a*), 14(*b*) and 14(*c*) are twisted to obtain an image of a twisted yarn shown in FIG. 14(*d*). It is clearly shown that fuzz 51 and 52 of a fancy yarn 50 shown in FIG. 14(*c*) is not reproduced on FIG. 14(*d*).

In FIG. 15, images of twisting yarns shown in FIGS. 15(*a*), 15(*b*), 15(*c*) and 15(*d*) are input to simulate images of twisted yarns shown in FIGS. 15(*e*), 15(*f*) and 15(*g*). In this manner, it is possible to simulate a twisted yarn in various combinations within a range of images of yarns that have been input.

When mask data such as hue, brightness, and saturation distributions relating to color of a yarn image is subjected to the twine rendering process, change of information relating to the color of the twisting yarn can be directly reflected on an image of the simulation result.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

INDUSTRIAL APPLICABILITY

As described above, according to the invention, in an image input step, images of a plurality of yarns used for twisting are input each in the form of an extended line, and in an abstracting step, abstracted model that extends in one direction and has a certain cross-section of a predetermined mathematizable shape is produced to abstract each of the yarns, and correspondence between each of the abstracted models and the images is set. The abstracted models of the plurality of yarns are twisted according to a predetermined condition to produce an abstracted model of a twisted yarn in a form extending along a central axis in a twisting step, and the abstracted model of the twisted yarn is projected onto a plane that is in parallel with the central axis in a projection step. In an image reproduction step, the images of the yarns are reproduced, based on the correspondence, on corresponding projected images of the abstracted models of the yarns included in the abstracted model of the twisted yarn that has been projected onto the plane. Thus, fine fuzz and so forth of each of the yarns is reproduced as an image, and an image that is close to the real can be created.

Furthermore, according to the invention, cross-section shapes of the plurality of yarns are abstracted as round shapes. An arrangement reference point is set, and the cross-section shapes of the abstracted models of the yarns are arranged around the arrangement reference point. A combination of the cross-section shapes is rotated around the central axis of the twisted yarn while the arrangement reference point is displaced along the central axis according to a predetermined condition. External shapes of the abstracted models of the yarns along the central axis of the twisted yarn are produced as a locus formed by rotating the cross-section shapes around the central axis. Thus, the three-dimensional model of the twisted yarn can be easily produced.

Furthermore, according to the invention, the yarns can be abstracted as flattened cross-section shapes.

Furthermore, according to the invention, a cross-section region around the arrangement reference point of the twisted yarn is divided in accordance with ratios of square roots of diameters obtained when the cross-sections of the abstracted models of the yarns are abstracted as round shapes, and the round cross-section shapes of the abstracted models of the yarns are flattened according to a predetermined condition in such a manner that the cross-section shapes of the adjacent yarns are in contact with each other on a boundary line between the divided regions. Thus, even an abstracted model of a twisted yarn obtained by twisting yarns having different thicknesses can be easily created.

Furthermore, according to the invention, even when the ratio of the square root of an abstracted model of one yarn occupies a half or more of an entire portion, adjustment is performed so that the abstracted model of this yarn occupies only a half of the cross-section region around the arrangement reference point. Thus, unrealistic simulation can be avoided in which a thick yarn occupies more than a half of the region around the arrangement reference point.

Furthermore, according to the invention, the arrangement reference point is set at a position different from the central axis of the twisted yarn, and the arrangement reference point is also rotated around the central axis of the twisted yarn. Thus, even when a thick yarn and a thin yarn are used in combination and the sizes of the region that is occupied by the yarns around the arraignment reference point cannot be made different, it is possible to make the state of the twisted yarn close to the real twisted yarn by displacing the central axis with respect to the arrangement reference point.

Furthermore, according to the invention, the central axis of the twisted yarn is set at a position that is obtained as an weighted average value obtained by weight-averaging relative positions of central positions of the cross-section shapes of the abstracted models of the yarns with respect to the arrangement reference point, using the diameters of the cross-section shapes as the weight. Thus, the twisted yarn can be well balanced with the central axis.

Furthermore, according to the invention, an abstracted model of a fuzzy yarn is produced separately for a fuzz portion on an outer circumferential side and for a yarn main portion on an inner circumferential side excluding the fuzz. The arrangement around the arrangement reference point is performed for the cross-section shape of the yarn main portion, and the cross-section shape of the fuzz portion is arranged around the cross-section shape of the yarn main portion not so as to exceed abstracted models of adjacent yarns. An image of the yarn is reproduced separately for the fuzz portion and for the yarn main portion from the image of the yarn. Thus, when a fuzzy yarn is used, fine fuzz in the twisted yarn cab be easily expressed.

Furthermore, according to the invention, the correspondence between the abstracted model and the image of each of the yarns is set so that with respect to a longitudinal direction of the abstracted model, an entire length or a part of the image is set to be a section to be used, and so that after linking is performed from one edge to the other edge of the section to be used, linking is repeated by resuming from the one edge. Thus, even when the length of a yarn that is input as an image is limited, it is possible to easily simulate the twisted yarn that is sufficiently long.

Furthermore, according to the invention, by using the image of the twisted yarn produced by reproducing the images of the yarns on the corresponding projected images of the abstracted models of the yarns included in the abstracted model of the twisted yarn projected on the plane, an image of a knitting fabric knitted by using the twisted yarn is simulated. Thus, not only can the twisted yarn be simulated, but also can an image of a knitting fabric using the twisted yarn be obtained.

Furthermore, according to the invention, an image of a twisted yarn can be simulated easily when the image is processed by a computer.

Furthermore, according to the invention, it is possible to easily let a computer read a stored program and simulate an image of a twisted yarn.

Furthermore, according to the invention, by image input means, images of a plurality of yarns used for twisting are input each in the form of an extended line, and by abstracting means, an abstracted model that extends in one direction and has a certain cross-section of a predetermined mathematizable shape is produced to abstract each of the yarns, and correspondence between each of the abstracted models and the images is set. Thus, an abstracted model of a twisted yarn can be easily created with the abstracted models obtained by abstracting the images of the real yarns by twisting means. The produced abstracted model of the twisted yarn is projected onto a plane that is in parallel with the central axis of the twisted yarn by projection means. By image reproduction means, a state in which the images of the yarns are reproduced, based on the correspondence that has been set by the abstracting means, on corresponding projected images of the abstracted models of the yarns included in the abstracted model of the twisted yarn is displayed. Thus, fine fuzz and so forth can be reproduced faithfully in the displayed image, and realistic simulation of the image can be performed.

Furthermore, according to the invention, the cross-section shapes of the plurality of yarns are abstracted as round shapes. An arrangement reference point with respect to the twisted yarn is set, and the cross-section shapes of the abstracted models of the yarns are arranged around the arrangement reference point and flattened according to a predetermined condition. A combination of the cross-section shapes is rotated around the central axis of the twisted yarn while the arrangement reference point is displaced along the central axis according to a predetermined condition. External shapes of the abstracted models of the yarns along the central axis of the twisted yarn are produced as a locus formed by rotating the cross-section shapes. Thus, the abstracted model of the twisted yarn can be obtained easily.

The invention claimed is:

1. A computer implemented method for simulating an image of a twisted yarn in which twisting of a plurality of yarns is simulated and an image of a twisted yarn is formed, the method comprising:
   an image input step of inputting images of the plurality of yarns used for twisting, each in a form of an extended line;
   an abstracting step of producing, based on the images that have been input in the image input step, an abstracted model of each of the yarns that extends in one direction and has a certain cross-section of a predetermined mathematizable shape to abstract each of the yarns, and of setting correspondence between each of the abstracted models and the images;
   a twisting step of twisting, according to a predetermined condition, the abstracted models of the plurality of yarns that have been abstracted in the abstracting step and of producing an abstracted model of a twisted yarn in a form extending along a central axis thereof;
   a projection step of projecting the abstracted model of the twisted yarn that has been produced in the twisting step onto a plane that is in parallel with the central axis; and
   an image reproduction step of reproducing, based on the correspondence that has been set in the abstracting step, the images of the yarns on corresponding projected images of the abstracted models of the yarns included in the abstracted model of the twisted yarn that has been projected onto the plane in the projection step.

2. The method for simulating an image of a twisted yarn of claim 1, wherein in the abstracting step, cross-section shapes of the plurality of yarns input in the image input step are abstracted as round shapes to produce the abstracted models of the yarns, and
   the twisting step comprises:
      a cross-section arrangement step of setting an arrangement reference point with respect to the twisted yarn, and of arranging the cross-section shapes of the abstracted models of the yarns produced in the abstracting step around the arrangement reference point;
      a cross-section rotation step of rotating a combination of the cross-section shapes arranged in the cross-section arrangement step around the central axis of the twisted yarn while displacing the arrangement reference point set in the cross-section arrangement step along the central axis, according to a predetermined condition; and
      an external shape production step of producing external shapes of the abstracted models of the yarns along the central axis of the twisted yarn as a locus formed by rotating the cross-section shapes in the cross-section rotation step.

3. The method for simulating an image of a twisted yarn of claim 2, wherein in the abstracting step, the cross-section shapes are flattened according to a predetermined condition.

4. The method for simulating an image of a twisted yarn of claim 2, wherein in the cross-section arrangement step, a cross-section region around the arrangement reference point of the twisted yarn is divided in accordance with ratios of square roots of diameters of the yarns in the abstracted models of the yarns and the round cross-section shapes of the abstracted models of the yarns are flattened in such a manner that the cross-section shapes of the adjacent yarns contact each other on a boundary line between the divided regions.

5. The method for simulating an image of a twisted yarn of claim 4, wherein in the cross-section arrangement step, when the ratio of the square root of diameter of yarn in an abstracted model of one yarn occupies a half or more of an entire portion, adjustment is performed so that the abstracted model of this yarn occupies only a half of the cross-section region around the arrangement reference point.

6. The method for simulating an image of a twisted yarn of claim 2, wherein the cross-section arrangement step, the arrangement reference point is set at a position different from the central axis of the twisted yarn, and
   in the cross-section rotation step, the arrangement reference point is also rotated around the central axis of the twisted yarn.

7. The method for simulating an image of a twisted yarn of claim 6, wherein in the cross-section arrangement step, the arrangement reference point is set in such a manner that the central axis of the twisted yarn is at a position that is obtained as an weighted average of relative positions of central positions of the cross-section shapes of the abstracted models of the yarns with respect to the arrangement reference point, using the diameters of the cross-section shapes as the weight.

8. The method for simulating an image of a twisted yarn of claim 2, wherein with respect to a fuzzy yarn,
   in the abstracting step, the abstracted model of the yarn is produced separately for a fuzz portion on an outer circumferential side and for a yarn main portion on an inner circumferential side excluding the fuzz,
   in the cross-section arrangement step, the abstracted model of the yarn is arranged around the arrangement reference point based on a cross-section shape of the yarn main portion, and a cross-section shape of the fuzz portion is arranged around the cross-section shape of the yarn main portion not so as to exceed abstracted models of adjacent yarns, and
   in the image reproduction step, an image of the yarn is reproduced on the abstracted model of the yarn projected on the plane separately for the fuzz portion and for the yarn main portion from the image.

9. The method for simulating an image of a twisted yarn of claim 1, wherein in the abstracting step, the correspondence between the abstracted model and the image of each of the yarns is set so that with respect to a longitudinal direction of the abstracted model, an entire length or a part of the image is set to be a section to be used, and so that after linking is performed from one edge to the other edge of the section to be used, linking is repeated by resuming from the one edge.

10. The method for simulating an image of a twisted yarn of claim 1, wherein by using the image of the twisted yarn produced by reproducing the images of the yarns on the abstracted models of the yarns included in the abstracted model of the twisted yarn projected on the plane in the image reproduction step, an image of a knitting fabric knitted by using the twisted yarn is simulated.

11. A computer-readable storage medium storing a program read by a computer to execute the method for simulating an image of a twisted yarn of claim 1.

12. An apparatus for simulating an image of a twisted yarn, in which twisting of a plurality of yarns is simulated and an image of a twisted yarn is formed, the apparatus comprising:

image input means for inputting images of the plurality of yarns used for twisting, each in a form of an extended line;

abstracting means for producing, based on the images that have been input in the image input means, an abstracted model of each of the yarns that extends in one direction and has a certain cross-section of a predetermined mathematizable shape to abstract each of the yarns, and for setting correspondence between each of the abstracted models and the images;

twisting means for twisting, according to a predetermined condition, the abstracted models of the plurality of yarns that have been abstracted in the abstracting means and of producing an abstracted model of a twisted yarn in a form extending along a central axis thereof;

projection means for projecting the abstracted model of the twisted yarn that has been produced in the twisting means onto a plane that is in parallel with the central axis; and image reproduction means for displaying a state in which the images of the yarns are reproduced, based on the correspondence that has been set by the abstracting means, on corresponding projected images of the abstracted models of the yarns included in the abstracted model of the twisted yarn that has been projected onto the plane by the projection means.

13. The apparatus for simulating an image of a twisted yarn of claim 12, wherein the abstracting means abstracts the cross-section shapes of the plurality of yarns input by the image input means as round shapes, and the twisting means comprises:

cross-section arrangement means for setting an arrangement reference point with respect to the twisted yarn, of arranging the cross-section shapes of the abstracted models of the yarns produced by the abstracting means around the arrangement reference point, and for flattening the cross-shapes according to a predetermined condition;

cross-section rotation means for rotating a combination of the cross-section shapes arranged by the cross-section arrangement means around the central axis of the twisted yarn while displacing the arrangement reference point set by the cross-section arrangement means along the central axis according to a predetermined condition; and external shape production means for producing external shapes of the abstracted models of the yarns along the central axis of the twisted yarn as a locus formed by rotating the cross-section shapes by the cross-section rotation means.

14. A computer-readable storage medium storing a program read by a computer to execute the method for simulating an image of a twisted yarn of claim 2.

* * * * *